(12) United States Patent
Mozdziak et al.

(10) Patent No.: US 7,663,019 B2
(45) Date of Patent: Feb. 16, 2010

(54) TRANSGENIC SNAKES AND METHODS OF MAKING

(75) Inventors: Paul E. Mozdziak, Raleigh, NC (US); James N. Petitte, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 18 days.

(21) Appl. No.: 11/752,599

(22) Filed: May 23, 2007

(65) Prior Publication Data

US 2008/0005807 A1  Jan. 3, 2008

Related U.S. Application Data

(60) Provisional application No. 60/802,985, filed on May 24, 2006, provisional application No. 60/829,060, filed on Oct. 11, 2006.

(51) Int. Cl.
*A01K 67/033* (2006.01)
*C12N 15/00* (2006.01)
*G01N 33/00* (2006.01)
*C12P 21/00* (2006.01)

(52) U.S. Cl. .............................. 800/13; 800/23; 800/25; 800/3; 800/4; 800/8

(58) Field of Classification Search .................. None
See application file for complete search history.

(56) References Cited

U.S. PATENT DOCUMENTS

| | | | |
|---|---|---|---|
| 3,069,314 A * | 12/1962 | Jenkins ........................ 424/40 |
| 5,925,803 A | 7/1999 | Leder et al. |
| 5,932,780 A | 8/1999 | Soreq et al. |
| 5,959,171 A | 9/1999 | Hyttinnen et al. |
| 6,166,288 A | 12/2000 | Diamond et al. |
| 6,204,431 B1 | 3/2001 | Prieto et al. |
| 6,255,554 B1 | 7/2001 | Lubon et al. |
| 6,339,183 B1 | 1/2002 | Sun |
| 6,344,596 B1 | 2/2002 | Velander et al. |
| 6,380,458 B1 | 4/2002 | Lin |
| 6,730,822 B1 | 5/2004 | Ivarie et al. |
| 7,098,031 B2 | 8/2006 | Choulika et al. |
| 7,176,345 B2 | 2/2007 | Kaelin, Jr. et al. |
| 2002/0157126 A1 | 10/2002 | Lee et al. |
| 2006/0101528 A1 | 5/2006 | Demeneix et al. |

OTHER PUBLICATIONS

Mozdziak et al. Status of Transgenic Chicken Models for Developmental Biology. Developmental Dynamics. 2004, vol. 229, pp. 414-421.*
Barnett, B, "Artificial Incubation of Reptile Eggs," Monitor—Journal of the Victorian Herpetological Society 9(2) 1998:4-8, Australia.
Clark, B, "Python Egg Incubation," Reptiles Magazine (Mar. 2006) pp. 1-6, www.bobclark.com/a03_06.asp, printed May 21, 2007.

* cited by examiner

*Primary Examiner*—Deborah Crouch
(74) *Attorney, Agent, or Firm*—Myers Bigel Sibley & Sajovec, P.A.

(57) ABSTRACT

A transgenic animal such as a transgenic snake or other reptile that expresses a heterologous expression product is described, along with methods of making the same. In general, the animal comprises cells containing a sequence encoding the heterologous expression product. The sequence encoding the heterologous expression product is integrated into the genome of the animal (e.g., in some or all cells thereof, and in some embodiments into germ cells thereof). The sequence encoding the heterologous expression product is, in general, operatively associated with an expression sequence or promoter. The animals are useful for, among other things, testing of repellents, testing of toxicological compounds, as teaching aids, for venom production, etc.

13 Claims, 5 Drawing Sheets

TRANSGENIC SNAKES AND METHODS OF MAKING

RELATED APPLICATIONS

This application claims the benefit of U.S. Provisional Patent Application No. 60/802,985; Filed May 24, 2006, and of U.S. Provisional Patent Application No. 60/829,060; Filed Oct. 11, 2006, the disclosures of both of which are incorporated by reference herein in their entirety.

FIELD OF THE INVENTION

The present invention is concerned with transgenic animals and the use thereof for (among other things) animal repellent screening, environmental and toxicological testing, production of therapeutic proteins, and classroom teaching aids.

BACKGROUND OF THE INVENTION

Since the initial introduction of transgenic animals as models for disease (see, e.g., U.S. Pat. No. 5,925,803 to Leder), transgenic animals have been found useful for a variety of different purposes.

Transgenic non-human mammals have been described for the production of therapeutic proteins of interest that can be collected from, for example, milk. See, e.g., U.S. Pat. Nos. 6,344,596; 6,339,183; 6,255,554; 6,204,431; 6,166,288; and 5,959,171.

Transgenic frogs have been described as useful for the detection of endocrine disrupters in the environment. See, e.g., US Patent Application Publication 2006/0101528, Transgenic frogs have also been described as a model for evaluating drug efficacy. See, e.g., U.S. Pat. No. 5,932,780.

Transgenic birds have been described as useful for, among other things, the production of exogenous proteins that can be collected from eggs laid by such birds. See, e.g., U.S. Pat. No. 6,730,822.

Transgenic zebrafish have been described as useful for developmental studies and the testing of toxic compounds, and as classroom teaching aids. See, e.g., U.S. Pat. No. 6,380,458. Transgenic zebrafish expressing a fluorescent protein are commercially available as the GLOFISH® from the Carolina Biological Supply Company (Burlington, N.C., USA).

Transgenic mice and certain other animals that express light-emitting fusion proteins are suggested for diagnostic and therapeutic purposes (e.g., drug screening and discovery) in W. Kaelin et al., U.S. Pat. No. 7,176,345.

SUMMARY OF THE INVENTION

Reptiles are a geographically widely dispersed group of animals with a number of interesting attributes, and accordingly represent an attractive population for the development of transgenic animals. Unfortunately, little work has been done to date in developing transgenic reptiles. Accordingly there is a need for new approaches to the production of transgenic reptiles, and particularly transgenic snakes.

The present invention provides a transgenic reptile, such as a transgenic snake, lizard, turtle, tortoise, or crocodilian. The reptile expresses a heterologous expression product. In general, the reptile comprises, consists of or consists essentially of cells containing a sequence encoding the heterologous expression product. The sequence encoding the heterologous expression product is integrated into the genome of the reptile (e.g., in some or all cells thereof, and in some embodiments into germ cells thereof). The sequence encoding the heterologous expression product is, in general, operatively associated with an expression sequence or promoter.

In some embodiment the expression product is a reporter protein such as a fluorescent or luminescent protein. In some embodiments the reptile has a phenotype of fluorescence or luminescence not found in the corresponding wild-type snake.

In some embodiments the expression product is a therapeutic protein. In some embodiments the therapeutic protein is expressed into albumin of eggs laid by the reptile (e.g., by expression in the oviduct or into ovalbumin).

In some embodiments the expression product is stable and transmitted through the germline thereof. In some embodiments the expression product is expressed in skin, muscle (e.g., skeletal muscle) or both.

The present invention is explained in greater detail in the drawings herein and the specification set forth below. The disclosures of all patent references cited herein are to be incorporated by reference herein in their entirety.

BRIEF DESCRIPTION OF THE DRAWINGS

FIG. 2 is a repeat of data presented in FIGS. 1 and 3. Lane 1, 1 kb ladder; Lane 2, Head—Dorsal A; Lane 3, Head—Ventral A; Lane 4, Mid-section—Dorsal A; Lane 5, Mid-section—Ventral A; Lane 6, Tail—Dorsal A; Lane 7, Tail—Ventral A Lane 8, Negative—$dH_2O$; Lane 9, Negative—Wild-type; Lane 10, Positive—pMIEM; Lane 11, Head—Dorsal B; Lane 12, Head—Ventral B; Lane 13, Mid-Section—Dorsal B; Lane 14, Mid-Section—Ventral B; Lane 15, Tail—Dorsal B; Lane 16, Tail—Ventral B; Lane 17, 1 kb ladder.

DETAILED DESCRIPTION OF THE PREFERRED EMBODIMENTS

Figure 1:
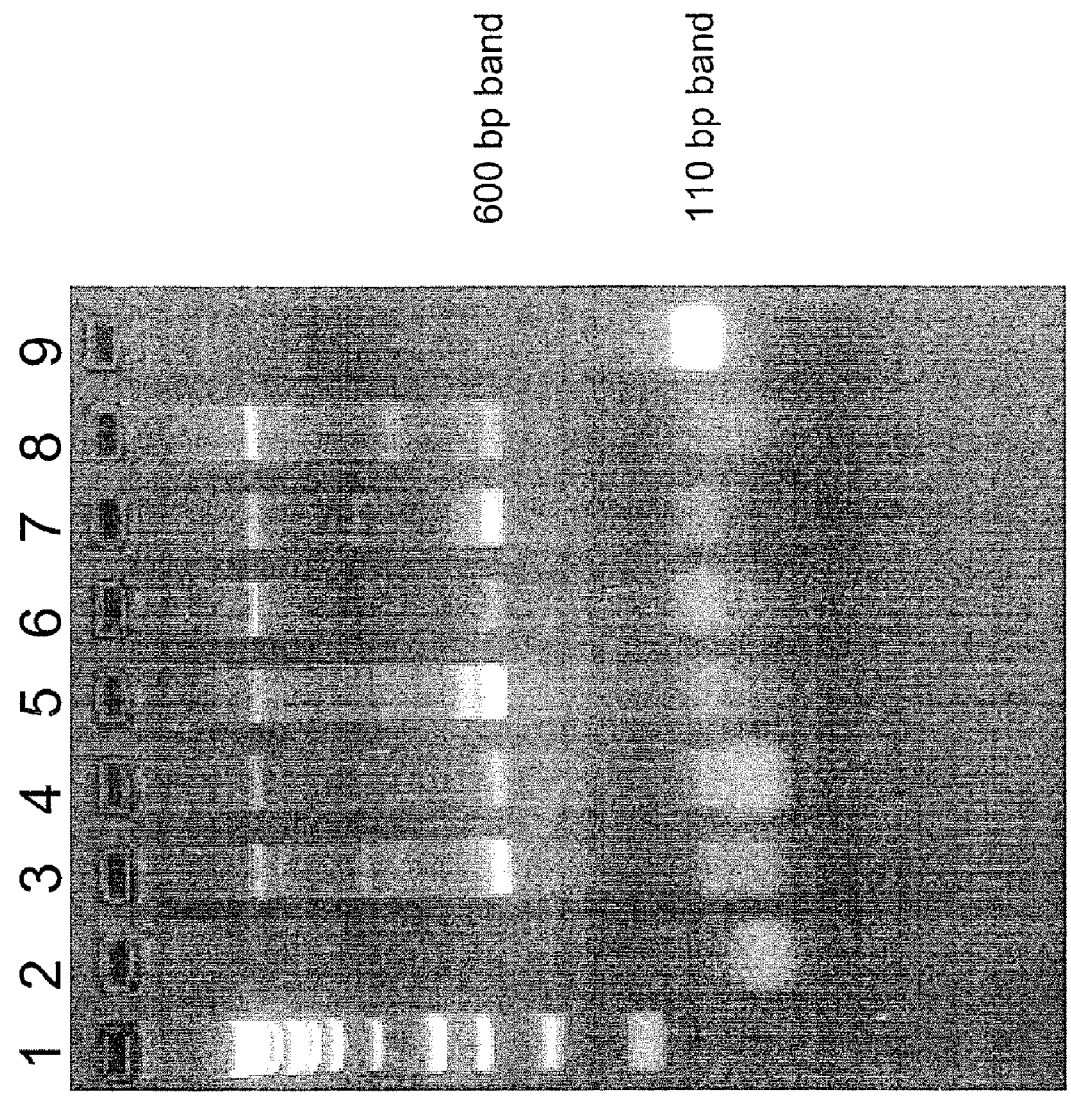
FIG. 1. Polymerase chain reaction (PCR) results from transgenic ball python skin. All samples indicate a predicted 118 base pair PCR product and a ~600 bp PCR product. Water control lane shows no amplification products. Lane 1, 1 kb ladder; Lane 2, negative control, $dH_2O$; Lane 3, Head—Dorsal; Lane 4, Mid-section—Dorsal; Lane 5, Tail—Dorsal; Lane 6, Head—Ventral; Lane 7, Mid-section—Ventral; Lane 8, Tail—Ventral; Lane 9, Positive control eGFP amplification.

"Reptile" as used herein includes animals of the class Sauropsida, and particularly animals of the orders Squamata (lizards, snakes and amphisbaenids (worm-lizards), Chelonia or Testudines (turtles) Crocodilia (crocodiles, caimans and alligators), and Rhynchocephalia (tuatars from New Zealand). Particularly preferred are snakes (suborder Serpente) and lizards (suborder Sauria).

"Snake" as used herein may be any snake, including snake families Boids, Colubridae, and Xenopeltidae (sunbeam snakes). Specific examples include but are not limited to *Python regius* (Ball Python), *Python molurus* (Burmese Python), *Python sebae* (African Rock Python), *Python reticulatus* (Reticulated Python), *Python curtus* (Blood Python), *Liasis mackloti* (Macklott's Python), *Antaresia maculosa* (Australian Spotted Python), *Antaresia childreni* (Childrens Python), *Morelia spilt* (Carpet Pythons), *Morelia viridis* (Green Tree Pythons), *Lampropeltis triangulum, Lampropeltis getulus, Lampropeltis mexicana, Lamorpeltis calligaster, Lamorpeltis doliata* (Scarlet King), *Lampropeltis alterna, Elaphe guttata* (Corn Snake), *Elaphe obsolete* (Rat Snake), *Elaphe vulpina* (Fox Snake), *Elaphe flavirufra* (Central American Rat Snake), *Elaphe bairdi* bairds (Rat Snake), *Bogertophis subocularis* (Trans-Pecos Ratsnake), *Bogertophis rosaliae* (Baja Ratsnake), *Elaphe Elena* (Trinket Snake), *Liasis fuscus* (Water Python), *Liasis olivaceus* (Olive Python), *Liasis papuanus* (Papuan Python), *Aspidites ramsayi* (Woma), *Aspidites elanocephalus* (Black Headed Python), *Pituophis Melanoleucus* (Pine Snake), *Pituophis Sayi* (Bull Snake), *Pituophis catenifer* (Gopher Snake), *Heterodon nasicus* (Western Hognose), *Heterodon platyrhinos* (Eastern Hognose), *Heterodon Simus* (Southern Hognose), *Xenopeltis hainanensis* (Sunbeam Snakes), and *Xenopeltis unicolor* (Sunbeam Snakes).

In some embodiments the snake is a colubrid snake such as a Kingsnake or milk snake, such as a common Kingsnake or *Lampropeltis getula* (e.g., California Kingsnake or *Lamropeltis getula californiae*; Eastern Kingsnake or *Lampropeltis getula getula*; Florida Kingsnake or *lampropeltis getulafloridana* etc.), or other members of the genus *Lampropeltis*.

"Lizards" as used herein may be any lizard, including but not limited to those of lizard families Iguanidae, Agamadae, Geckonidae, Varanidae, and Teiidae. Specific examples include but are not limited to: *Iguana iguana* (Green Iguana), *Cyclura nubila* or *Cyclura lewisi* (Blue Iguana), *Varanus exanthamaticus* (Savannah Monitor), *Varanus niloticus* (Nile Monitor), *Varanus salvator* (Water Monitor), *Varanus prasinus* (Tree Monitor), *Varanus indicus* (Indian Monitor), *Varanus salvator* (Water Monitor), *Gekko gecko* (Tokay Gecko), *Eublepharis macularius* (Leopard Gecko), *Eublepharis Hemitheconyx* (Fat tailed Gecko), *Gekko ulikovski* (Golden Gecko), *Paroedura pictus* (Madagascar Ground Gecko), *Phelsuma abboti* (Day Gecko), *Naultinus elegans* (Green Tree Gecko), *Pogona Vitticeps* (Bearded Dragons), *Tupinambis teguixin* (Tegu), *Tupinambis merianae* (Blue Tegu), *Tiliqua scincoides* (Skinks), *Varanus indicus* (Indian Monitor), *Anolis carolinensis* (Green Anole), *anolis sagrei* (Brown Anole), *Anolis equestris* (Knight Anole), *Anolis ricordii* (Giant Anole), and *Chamaelo calyptratus* (Veiled Chameleon)

"Turtle" as used herein may be any turtle as discussed above, with particular examples including but not limited to: *Trachemys scripta* (Sliders), *Chrysemys picta* (Painted Turtle), *Graptemys geographica* (Common Map Turtle), *Graptemys pulchra* (Alabama Map Turtle), *Graptemys versa* (Texas Map Turtle), *Apalone ferox* (Florida Softshell Turtle), *Apalone mutica* (Smooth Softshell Turtle), and *Apalone spinifera* (Spiny Softshell Turtle).

"Tortoise" as used herein includes but is not limited to tortoise families Testudinidae, Emydidae, and Trionychidae, with particular examples including but not limited to: *Geochelone carbonaria* (Red-Footed Tortoise), *Geochelone denticulata* (South American yellow-footed tortoise), *Geochelone radiata* (Radiated tortoise, *Geochelone sulcata* (African Spurred Tortoise), *Geochelone pardalis* (Leopard Tortoise), and *Testudo horsfieldii* (Russian Tortoise).

"Crocodilian" as used herein may be any crocodilian species, including those in families Crocodyles and Crocodylidae, with particular examples including but not limited to *Caiman crocodilus* (Spectacled Caiman), *Alligator mississippiensis* (American Alligator), and *Osteolaemus tetraspis* (African Dwarf Crocodile).

"Retroviral vectors" and "lentiviral vectors" useful for carrying out the present invention are known. In general such vectors comprise a viral particle enclosing viral nucleic acid which has been modified to incorporate the nucleic acid of interest to be carried into the target animal cells. Such vectors may be produced from the nucleic acids of any suitable virus, including but not limited to the human immunodeficiency virus, feline immunodeficiency virus, equine infection anemia virus, Moloney murine leukemia virus, etc. Where the host specificity of a vector is not appropriate for the target cells of the present invention that specificity may be changed to render it suitable for the present invention by the technique of pseudotyping as discussed below.

"Pseudotyped retroviral vectors" and "pseudotyped lentiviral vectors" as used herein are known. In general such vectors are those in which a viral capsid is changed, a viral capsid protein is replaced, an additional viral capsid protein is added, etc., to change, alter, or broaden the cell specificity of the virus so that it is internalized by the desired target. Pseudotyped retroviral vectors are known.

"Expression sequence" as used herein typically refers to at least one promoter, enhancer, response element, or combination thereof, including the response elements ordinarily associated with the corresponding promoter and response elements from different promoters. Promoters, enhancers and response elements may be obtained from any suitable species, including reptile, amphibian (e.g., frog), avian (e.g., chicken), and mammalian species (e.g., mouse), as well as from viruses.

"Therapeutic protein" as used herein may be any protein (including peptide, active protein fragments, and fusion proteins thereof) that has therapeutic utility in treating human or animal disease. Examples include but are not limited to insulin, glucagon-like peptide 1, antibodies, histocompatibility antigens, integrins, selectin inhibitors, growth factors, postridical hormones, nerve growth hormones, blood clotting factors, adhesion molecules, bone morphogenic proteins, lectins, trophic factors, cytokines such as TGF-beta, IL-2, IL-4, alpha-IFN, beta-IFN, gamma-IFN, TNF, IL-6, IL-8, lymphotoxin, IL-5, Migration inhibition factor, GMCSF, IL-7, IL-3, monocyte-macrophage colony stimulating factors, granulocyte colony stimulating factors, multidrug resistance proteins, other lymphokines, toxoids, erythropoietin, Factor VIII, amylin, TPA, dornase-alpha, alpha-1-antitrypsin, human growth hormones, nerve growth hormones, bone morphogenic proteins, growth differentiation factors, neuregulin, urease and toxoids, and active fragments thereof, active peptides, and fusion proteins thereof. (see, e.g., US Patent Application Publication No. 2006/0008532), as well as all of the therapeutic proteins listed in Table 1 of U.S. Pat. No. 6,946,134 and fusion proteins thereof.

"Reporter protein" as used herein includes but is not limited to pigment proteins, fluorescent proteins, luminescent protein, enzymes and other detectable proteins. Specific examples include but are not limited to melanin (including eumalanin and pheomelanin), carotenoids, pteridines, cyan biochromes, aequorin, luciferase, luciferin, blue fluorescent protein, red fluorescent protein, ds red fluorescent protein, cyan fluorescent protein, yellow fluorescent protein, and green fluorescent protein (including naturally occurring and mutant variants thereof). See, e.g., U.S. Pat. Nos. 7,034,141; 7,037,645; and 6,087,476. In some embodiments the visually detectable proteins such as the fluorescent or luminescent proteins are preferred. The foregoing is to be construed as inclusive of "enhanced" proteins, including but not limited to enhanced green fluorescent protein (eGFP), which are known in the art.

"Fluorescent or luminescent" as used herein to describe an animal phenotype means that at least a portion of the animal is visibly fluorescent or luminescent to the ordinary human observer under usual conditions for observing fluorescence or luminescence (e.g., dimmed or reduced light, as in night-time or a darkened room, with or without the addition of supplemental illumination of the animal with an ultra-violet or "black" light). The phenotype may be exhibited as a pattern of fluorescence or luminescence on or through the skin of the animal, overall fluorescence or luminescence on or through the skin of the animal, and/or fluorescence or luminescence of the eyes of the animal, etc.

A. Nucleic Acid Constructs and Vectors.

Heterologous nucleic acids of interest (e.g., those encoding a therapeutic, detectable or reporter protein) can be operatively associated with expression sequences operative in animals of the invention and inserted into suitable vectors for infection animal cells of the invention in accordance with known techniques, or variations thereof that will be apparent to those skilled in the art. See, e.g., U.S. Pat. Nos. 6,730,822; 6,380,458; and 5,932,780; see also US Patent Application Publication No. 2006/010528.

Retroviral and lentiviral vectors are known. See, e.g., U.S. Pat. Nos. 6,949,242; 6,838,280; 6,323,195; 6,303,116; 6,107,478; and 4,980,286. Where the vectors are replication deficient they can be produced in helper cell lines in accordance with known techniques. See, e.g., U.S. Pat. Nos. 6,712,612; 5,124,263; 4,861,719; and 4,650,764. Pseudotyped vectors are known and retroviral and lentiviral vectors can be pseudotyped in accordance with known techniques. See, e.g., U.S. Pat. Nos. 6,863,884; 6,849,454; 6,544,779; 6,479,281; 6,117,681; 5,739,018; 5,670,354; and 5,512, 421; see also J. Yee et al., Generation of high-titer pseudotyped retroviral vectors with very broad host range, *Methods Cell Biol.* 43, 99-112 (1994); J. Burns et al., Vesicular stomatitis virus G glycoprotein pseudotyped retroviral vectors: Concentration to very high titer and efficient gene transfer into mammalian and nonmammalian cells, *Proc. Natl Acad. Sci. USA* 90, 833-8037 (September 1993). In some embodiments, Vesicular stomatitis virus G glycoprotein (VSV-G) pseudotype retroviral and lentiviral vectors are preferred.

Expression sequences comprising promoters, enhancers, response elements and combinations thereof (sometimes referred to as "regulatory elements") useful for carrying out the present invention are known. See, e.g., U.S. Pat. Nos. 6,730,822; 6,380,458; and 5,932,780. The expression sequences may be constitutively active or inducible (e.g., tissue-specific). Examples include but are not limited to the CMV promoter, beta-actin promoter, the RSV promoter, crystallin promoters such as the alpha and delta crystallin promoters, the mylz2 promoter, the PGK promoter, the myosin heavy chain promoter, the myosin light chain promoter, the cardiac myosin promoter, and the keratin promoter. See, e.g., U.S. Pat. Nos. 6,949,242; 6,897,045; and 6,784,289. In some embodiments crystallin promoters and/or enhancers, such as the delta crystallin promoter and/or enhancers, are preferably included in the expression sequence. See, e.g., L. Reneker et al., *Invest. Opthalmol. Vis. Sci.* 45, 4083-90 (2004); X. Li et al., *Dev. Genet.* 20, 258-66 (1977). In some embodiments, where expression of a desired protein such as a therapeutic protein into eggs of transgenic reptiles for subsequent harvesting is desired, ovalbumin promoters may be used. See, e.g., U.S. Pat. No. 6,730,822.

A nucleic acid encoding the expression product (sometimes also referred to as a protein of interest) is operatively associated with the expression sequence to form what is sometimes referred to as an "expression cassette" in accordance with known techniques. If desired, insulators can be included upstream, downstream, or both upstream and downstream from the expression sequence and associated nucleic acid encoding the expression product, in accordance with known techniques. See, e.g., U.S. Pat. Nos. 6,395,549; 6,229, 070; 6,100,448; and 5,610,053. Also if desired, scaffold attachment regions can be included upstream, downstream, or both upstream and downstream from the expression sequence and associated nucleic acid encoding the expression product, in accordance with known techniques. See, e.g., U.S. Pat. Nos. 6,239,328; 6,100,448; 5,773,695; and 5,773,689.

Vector particles containing vector nucleic acid with the with inserted expression cassette is preferably concentrated in its injection solution (e.g., its growth media), for example to a titre of $10^7$ to $10^9$ infectious units per milliliter of injection solution. A cationic polymer such as 1,5-dimethyl-1,5-diaza-undecamethylene polymethobromide, hexadimethrine bromide (commercially available as POLYBRENE® from Sigma Aldrich) may be added to the injection solution to enhance retroviral infection of the target cells, in accordance with known techniques (See, e.g., J. Manning et al., *Appl. Microbiol.* 22,1162 (1971)).

B. Egg Injection and Incubation.

Freshly laid reptile eggs are available from a variety of sources, including Bob Clark Captive Bred Reptiles Inc., 12316 Val Verde Drive, Oklahoma City, Okla. 73142 (telephone (405) 722-5017), Prehistoric Pets, 18822 Brookhurst St., Fountain Valley, Calif., 92708 (telephone (714) 964-3525), and collection from the wild.

Unlike bird eggs, reptile eggs appear to be position sensitive to their site of injection and incubation. Hence, freshly laid reptile eggs are preferably marked to indicate the position at which they were laid by any suitable means (for example, a pen or pencil marking such as an "x" at the uppermost laid position thereof is suitable). The eggs can then be collected for vector administration.

Unlike bird eggs, reptile eggs rapidly absorb or release water from the atmosphere or their environment (in some cases, particulate media such as vermiculite particulate media). Hence the contents of reptile eggs are at a positive pressure relative to the ambient atmosphere under conditions of high humidity. To avoid excess leakage of egg contents after injection, the eggs are preferably slightly dried prior to injection to reduce the internal pressure therein. Drying may be carried out by simply placing the eggs in a dry ambient environment or a dry particulate media for a suitable duration, e.g., from five minutes to one day or more (e.g., about one hour for a python egg; about one day for a corn snake egg).

After drying the egg may then be injected. Injection may be carried out with the aid of a dissection microscope with supplemental illumination such as by fiber optic illumination, with injection being made into a region such as the embryo proper or a blood vessel associated with the embryo. Injection is preferably carried out with a fine needle such as a 30 gauge needle, with an injection volume of from 50 to 1000 microliters of concentrated vector-containing injection solution typically being appropriate, depending upon factors such as the concentration of the solution, the size of the embryo, whether or not cationic polymer is included, etc. The eggs are preferably injected within one or two days of being laid.

Since (unlike bird eggs) reptile eggs are leathery in texture, injection may be carried out directly through the shell without prior fracturing of the shell.

After injection the injection needle should be withdrawn slowly and after needle withdrawal the injection hole is preferably immediately and rapidly sealed with rubber cement or other suitable sealant to prevent albumin from leaking through the hole (which would provide a site for opportunistic infection of the egg during subsequent incubation).

After injection the eggs are placed in an incubator. Unlike bird eggs, the reptile eggs should preferably be positioned in the incubator in a position that corresponds to the position in which they were originally laid (which may be identified by any suitable means such as a marking at the uppermost portion thereof as noted above).

Reptile eggs are preferably incubated in or on a particulate media such as vermiculite particulate media. The media is preferably dampened with the addition of water during incubation. Depending upon the species, the eggs may be completely buried in the particulate media, partially buried in the particulate media, or allowed to rest on top of the particulate media.

Also, unlike bird eggs which are "rocked" during incubation, reptile eggs should preferably be incubated without rocking, and are preferably maintained as motionless as possible during their incubation to avoid tearing of or mechanical damage to the embryo (note that reptile embryos are attached to the interior of their shell while bird embryos are not). Reptile eggs are incubated for a relatively long time as compared to bird eggs, with incubation times of two months being typical. In addition, reptile eggs are incubated at a relatively low temperature as compared to bird eggs, with incubation temperatures of 65 to 78 degrees Fahrenheit (and in some cases up to 95 degrees Fahrenheit) being typical.

Procedures for the artificial incubation of reptile eggs are described in, among other sources, B. Barnett, Artificial Incubation of Reptile Eggs, *Monitor—Journal of the Victorian Herpetological Society* 9(2): 4-8 (1998) and B. Clark, Python Egg Incubation, *Reptiles Magazine* (March 2006).

C. Hatching and Subsequent Propagation.

Unlike chicks, reptiles upon hatch will tend to stay in their broken shells for a period of time (e.g., several days). The reptiles should preferably be allowed to remain in their shells until they emerge of their own accord and not forcibly removed.

First generation reptiles of the invention produced by injection with vector and incubation to hatch as described above will typically be chimeric, in that some cells of the reptiles will contain and express the heterologous nucleic acid while other cells will not. A portion of such first generation reptiles will include germ-line transformed animals in which the heterologous nucleic acid is incorporated into germ cells and can be passed to or inherited by subsequent generations. If desired, such germ-line transformed reptiles can be bred with other reptiles, including wild-type reptiles or other genetically modified reptiles, to produce second generation reptiles of the invention in which all or essentially all cells contain the heterologous nucleic acid integrated into the genome thereof. Second generation reptiles of the invention can in turn be propagated in accordance with known techniques.

Reptiles of the invention subsequent to the first generation may be heterozygous or homozygous for the heterologous nucleic acid, depending upon the choice of parents, as is known in the art.

First or subsequent generation reptiles of the invention in some embodiments exhibit the phenotype of fluorescence or luminescence.

First or subsequent generation reptiles of the invention in some embodiments exhibit the phenotype of expressing a heterologous protein such as a therapeutic protein in eggs (e.g., into egg albumin) that are laid by those reptiles.

In one embodiment of the invention, a first or subsequent generation reptile of the invention as a first (male or female) parent is crossed with an albino or reduced-pigment reptile (e.g., a leucistic reptile such as a leucistic snake of any of the species noted above, leucistic ball snake) of the same species so that progeny or subsequent generation reptiles are produced that exhibit both the fluorescent or luminescent phenotype and the albino or leucistic phenotype in combination.

First and subsequent generation reptiles of the invention express the expression product in at least one of a desired tissue, including but not limited to skin, muscle such as skeletal muscle, in the oviduct (e.g., for secretion of a therapeutic product into the albumin for subsequent harvesting). See, e.g., U.S. Pat. No. 6,730,822.

Reptiles for breeding with transgenic reptiles of the invention are available from a variety of sources, including Bob Clark Captive Bred Reptiles Inc., Prehistoric Pets, and collection from the wild.

D. Utility.

Reptiles of the invention (including snakes, lizards, and crocodilians) are useful for testing for toxic, teratogenic, and/or oncogenic agents in a manner analogous to the GLOFISH® fluorescent zebrafish or transgenic frogs. Reptiles of the invention are particularly useful for testing the effects, at various concentrations and under various conditions emulating their natural environment, of androgens, estrogens, other endocrine disrupters, and pesticides, as such compounds may be found in the environment in which reptiles ordinarily reside.

Reptiles are utilized as test subjects for the identification of reptile repellents as described in U.S. Pat. No. 6,689,397 to Clark. In Clark et al. a potential repellant is sprayed directly onto the snake and the behavior of the snake thereafter observed (e.g., for locomotor or escape behavior). Reptiles of the present invention (including snakes, lizards, and crocodilians such as crocodiles and alligators), particularly those that express a fluorescent or luminescent protein, can be utilized in like manner, with the behavior of the reptile more readily observed due to the enhanced visibility of the test subject. In an alternate embodiment, since reptiles of the invention are in some embodiments more readily observed, the need for spraying a potentially noxious compound on the reptile is obviated and instead the potential repellant can be applied to a target or locus positioned in proximity to the reptile and the behavior of the reptile in relation to the target (e.g., frequency of approach or avoidance as compared to a like target to which the potential repellant has not been applied) then observed. Further, such tests can be carried out in an environment more natural to the animal, (such as a pond, penned marsh, grassy or wooded area, etc.) so that the test is both less noxious to the animal and a more realistic indicator of actual efficacy of the proposed repellant.

Venomous reptiles (including snakes) are maintained for the production of venom which is used commercially as a biomedical testing reagent and to produce antivenin. Reptiles of the invention that express a visually detectable product (and are venomous) are useful for such purposes to facilitate the handling and retrieval of such reptiles.

Transgenic reptiles of the invention that express a therapeutic protein of interest are useful for the production and subsequent harvesting of the therapeutic protein. Such therapeutic proteins may be collected by any suitable means. In a preferred embodiment, where the therapeutic protein is expressed into albumin of eggs laid by transgenic reptiles of the invention, the therapeutic protein may be collected, isolated and purified directly from the albumin in accordance with known techniques such as described in U.S. Pat. No. 6,730,822. Pythons, which lay relatively large eggs, are particularly useful for this purpose.

Reptiles raised or maintains as pets, as teaching aids, for venom production, and as test subjects occasionally escape. For example, when a reptile is used to test environmental contaminants it may be placed in a several acre pen or pond containing a significant amount of natural area. When they escape it is desirable to catch and retrieve escaped animals rather than permit their ultimate escape to the wild. Transgenic reptiles of the invention that carry and express a transgene encoding a detectable protein are accordingly useful to hobbyists, as well as researchers studying toxicology, teratology and oncology, in that they provide subjects hat can be more easily retrieved in the event of escape.

Since reptiles of the invention are more easily retrievable upon escape than their wild-type counterparts, reptiles of the invention are more readily housed in larger, more natural or wild-type pens that more closely emulates their natural environment when they are maintained for purposes such as testing, venom production, etc.

Reptiles of the invention are commercially desirable by collectors, hobbyists and pet owners, such as those organized under various hobbyist and herpetological societies such as The Center for North American Herpetology (1502 Medinah Circle, Lawrence, Kans. 66047 USA), the Philadelphia Herpetological Society, the Tucson Herpetological Society, the Arizona Herpetological Association, etc.

Reptiles of the invention are useful as subjects or animal actors in the film industry, which use should be carried out in accordance with American Humane's *Guidelines for the Safe Use of Animals in Filmed Media* (available from American Humane Film and Television Unit, 15366 Dickens Street, Sherman Oaks, Calif. 91403 USA (telephone (818) 501-0123).

Since the reptile brain is less highly developed than the brain of mammalian species such as mice, rats, and rabbits, transgenic reptiles of the invention provide, in some instances, a preferable alternative as research subjects in those situations where research subjects are necessary for biomedical research and toxocologic, teratologic, drug discovery, and oncogenic testing. See, e.g., U.S. Pat. No. 7,176,345 to Kaelin et al.

The present invention is explained in greater detail in the following non-limiting examples.

Example 1

Preparation of MMLV Retroviral Vector

A DNA construct of, from 5' to 3', the Rous sarcoma virus promoter, the chicken beta-actin promoter, the chicken delta crystallin enhancer, and DNA encoding enhanced green fluorescence protein, was prepared. The construct has the sequence between the Sadl and Pacl restriction sites in the plasmid given in Table 1 below.

Briefly, a plasmid encoding the Rous sarcoma virus (RSV) promoter, the chicken beta-actin promoter, the chicken delta crystallin enhancer, and DNA encoding enhanced green fluorescence protein built on a pUC backbone, was cut with the restriction enzymes Sacl and Pacl as shown in Table 1 below to specifically fractionate the portion of the plasmid encoding the Rous sarcoma virus (RSV) promoter, the chicken beta-actin promoter, the chicken delta crystallin enhancer, and enhanced green fluorescence protein. Subsequently, the DNA fragment was ligated into the pFB plasmid (Stratagene, La Jolla Calif.). Subsequently, the plasmid was transfected into 293T retroviral packaging cells using lipofectamine-2000 (Invitrogen, Carlsbad Calif.) with pVPack-env plasmid encoding the viral coat proteins and pVpack GP encoding the viral gag and pol genes (Stratagene, LaJolla, Calif.). Retroviral supernatant was collected from the cultures.

Similarly, the fragment encoding the Rous sarcoma virus (RSV) promoter, the chicken beta-actin promoter, the chicken delta crystallin enhancer, and enhanced green fluorescence protein was ligated into the pCDF1-MCS1™ lentiviral cloning vector (System Bio, Mountain View Calif.). The plasmid was transfected into 293T cells using lipfectamine-2000 with pPACKF1 Lentivector Packaging Kit that contained plasmids that provide the lentiviral coat proteins and the viral gag and pol genes (System Bio, Mountain View Calif.). Tissue culture supernatant was collected from the cultures.

TABLE 1 pMIEM (1 bp-4760 bp, direct) 4760 bp'

CAGTGGGGTTGGCACTGCCACGCTCCGGATGCCGCGCTCTGATCCAACCCCATAATCAAGGGAACCCGAA

TTGCCCCATCATTGCCCCCACCACCCCCATCCTGCCGGGCCCTCACACCCCACGCTGCCTTCTGGTGACA

TTCCCCAGCCCAAACCCACGGCTTCATGGCTACCGCGGGGCATTTCCCATTGCCGCCCCATTATCAGCTC

TGCACACCTCCCGCTGTACCCATGCCTCGTGGCTGCCCTTCTTTGACGTATAATCTTCTAATTAATACCC

GGCCTTGTCAAAGTGGAGCACAAACGTTAATTAATTCCCCAGCAGGCAGGTAATTAACACTGTGACTCCC

TTTTTGCTGCGAGTGGGGCTGATACAGAGAGATGTGGCACTATGGAGCCCACGGGGTCCTGGCACTGGGT

GCCCACGGAGGTCCCCATGTGCAGCTTGGGAGCTTGGGCCCAGCTGCTCCCTGCTTGTGTGTTGGAGGTC

TABLE 1-continued pMIEM (1 bp-4760 bp, direct) 4760 bp'

GCTGAGTAGTGCGCGAGCAAAATTTAAGCTACAACAAGGCAAGGCTTGACCGACAATTGCATGAAGAATC

TGCTTAGGGTTAGGCGTTTTGCGCTGCTTCGCGATGTACGGGCCAGATATACGCGTATCTGAGGGGACTA

GGGTGTGTTTAGGCGAAAAGCGGGGCTTCGGTTGTACGCGGTTAGGAGTCCCCTCAGGATATAGTAGTTT

CGCTTCTGCATAGGGAGGGGGAAATGTAGTCTTATGCAATACTCTTGTAGTCTTGCAACATGGTAACGAT

GAGTTAGCAACATGCCTTACAAGGAGAGAAAAAGCACCGTGCATGCCGATTGGTGGAAGTAAGGTGGTAC

GATCGTGCCTTATTAGGAAGGCAACAGACGGGTCTGACATGGATTGGACGAACCACTGAATTCCGCATTG

CAGAGATATTGTATTTAAGTGCCTAGCTCGATACAATAAACGCCATTTGACCATTCACCACATTGGTGTG

CACCTCCCAAGCTGCTCAGTGCATGCACGCTCATTGCCCATCGCTATCCCTGCCTCTCCTGCTGGCGCTC

CCCGGGAGGTGACTTCAAGGGGACCGCAGGACCACCTCGGGGGTGGGGGAGGGCTGCACACGCGGACCC

CGCTCCCCCTCCCCAACAAAGCACTGTGGAATCAAAAAGGGGGAGGGGGATGGAGGGGCGCGTCACAC

CCCCGCCCCACACCCTCACCTCGAGGTGAGCCCCACGTTCTGCTTCACTCTCCCCATCTCCCCCCCCTCC

CCACCCCCAATTTTGTATTTATTTATTTTTTAATTATTTTGTGCAGCGATGGGGCGGGGGGGGGGGG

CGCGCGCCAGGCGGGGCGGGGCGGGGCGAGGGGCGGGGCGGGGCGAGGCGGAGAGGTGCGGCGGCAGCCA

ATCAGAGCGGCGCGCTCCGAAAGTTTCCTTTTATGGCGAGGCGGCGGCGGCGGCGGCCCTATAAAAAGCG

AAGCGCGCGGCGGGCGGGAGTCGCTGCGCGCTGCCTTCGCCCCGTGCCCCGCTCCGCCGCCGCCTCGCGC

CGCCCGCCCCGGCTCTGACTGACCGCGTTACTCCCACAGGTGAGCGGGCGGGACGGCCCTTCTCCTCCGG

GCTGTAATTAGCGCTTGGTTTAATGACGGCTCGTTTCTTTTCTGTGGCTGCGTGAAAGCCTTAAAGGGCT

CCGGGAGGGCCCTTTGTGCGGGGGGGAGCGGCTCGGGGGTGCGTGCGTGTGTGTGCGTGGGGAGCGC

CGCGTGCGGCTCCGCGCTGCCCGGCGGCTGTGAGCGCTGCGGGCGCGGCGCGGGGCTTTGTGCGCTCCGC

AGTGTGCGCGAGGGGAGCGCGGCCGGGGGCGGTGCCCCGCGGTGCGGGGGGGCTGCGAGGGGAACAAAGG

CTGCGTGCCGGGGTGTGTGCGTGGGGGGGTGAGCAGGGGGTGTGGGCGCGGCGGTCGGGCTGTAACCCCC

CCCTGCACCCCCCTCCCCGAGTTGCTGAGCACGGCCCGGCTTCGGGTGCGGGGCTCCGTGCGGGGCGTGG

CGCGGGGCTCGCCGTGCCGGGCGGGGGTGGCGGCAGGTGGGGGTGCCGGGCGGGGCGGGGCCGCCTCGG

GCCGGGGAGGGCTCGGGGGAGGGGCGCGGCGGCCCCCGGAGCGCCGGCGGCTGTCGAGGCGCGCGAGCC

GCAGCCATTGCCTTTTATGGTAATCGTGCGAGAGGGCGCAGGGACTTCCTTTGTCCCAAATCTGTGCGGA

GCCGAAATCTGGGAGGCGCCGCCGCACCCCCTCTAGCGGGCGCGGGGCGAAGCGGTGCGGCGCCGGCAGG

AAGGAAATGGGCGGGAGGGCCTTCGTGCGTCGCCGCCGCCGTCCCCTTCTCCATCTCCAGCCTCGGG

GCTGTCCGCAGGGGACGGCTGCCTTCGGGGGGACGGGGCAGGGCGGGGTTCGGCTTCTGGCGTGTGAC

CGGCGGGGTTTATATCTTCCCTTCTCTGTTCCTCCGCAGCCCCCAAGCTCCCACAGTTTTACTTGAATGT

GGCACTGAGAGATTTTTAGGAGAATATATCAATAATGCATTTGAACATATCCTTTAATTTTAATTACTCT

CAGGGGGATAAACTTTTGGGAGGAAGATTTGTTGGAAGCACAGATCCCATCATGGAGATTCTCAGCTCTT

CTATATCCACTGAGCAGAGACTGACTGAAGTTGATGGGGATCGGGATCCACCGGTCGCCACCATGGTGAG

CAAGGGCGAGGAGCTGTTCACCGGGGTGGTGCCCATCCTGGTCGAGCTGGACGGCGACGTAAACGGCCAC

AAGTTCAGCGTGTCCGGCGAGGGCGAGGGCGATGCCACCTACGGCAAGCTGACCCTGAAGTTCATCTGCA

CCACCGGCAAGCTGCCCGTGCCCTGGCCCACCCTCGTGACCACCCTGACCTACGGCGTGCAGTGCTTCAG

CCGCTACCCCGACCACATGAAGCAGCACGACTTCTTCAAGTCCGCCATGCCCGAAGGCTACGTCCAGGAG

CGCACCATCTTCTTCAAGGACGACGGCAACTACAAGACCCGCGCCGAGGTGAAGTTCGAGGGCGACACCC

TGGTGAACCGCATCGAGCTGAAGGGCATCGACTTCAAGGAGGACGGCAACATCCTGGGGCACAAGCTGGA

TABLE 1-continued pMIEM (1 bp-4760 bp, direct) 4760 bp'

```
GTACAACTACAACAGCCACAACGTCTATATCATGGCCGACAAGCAGAAGAACGGCATCAAGGTGAACTTC
AAGATCCGCCACAACATCGAGGACGGCAGCGTGCAGCTCGCCGACCACTACCAGCAGAACACCCCCATCG
GCGACGGCCCCGTGCTGCTGCCCGACAACCACTACCTGAGCACCCAGTCCGCCCTGAGCAAAGACCCCAA
CGAGAAGCGCGATCACATGGTCCTGCTGGAGTTCGTGACCGCCGCCGGGATCACTCTCGGCATGGACGAG
CTGTACAAGTAAAGCGGCCGCGACTCTAGATCATAATCAGCCATACCACATTTGTAGAGGTTTTACTTGC
TTTAAAAAACCTCCCACACCTCCCCCTGAACCTGAAACATAAAATGAATGCAATTGTTGTTGTTAACTTG
TTTATTGCAGCTTATAATGGTTACAAATAAAGCAATAGCATCACAAATTTCACAAATAAAGCATTTTTTT
CACTGCATTCTAGTTGTGGTTTGTCCAAACTCATCAATGTATCTTAAGGCGTAAATTGTAAGCGTTAATG
ATCCCCGGGTACCGAGCTCGAATTCGTAATCATGTCATAGCTGTTTCCTGTGTGAAATTGTTATCCGCTC
ACAATTCCACACAACATACGAGCCGGAAGCATAAAGTGTAAAGCCTGGGGTGCCTAATGAGTGAGCTAAC
TCACATTAATTGCGTTGCGCTCACTGCCCGCTTTCCAGTCGGGAAACCTGTCGTGCCAGCTGCATTAATG
AATCGGCCAACGCGCGGGGAGAGGCGGTTTGCGTATTGGGCGCTCTTCCGCTTCCTCGCTCACTGACTCG
CTGCGCTCGGTCGTTCGGCTGCGGAATGAATCGGCCAACGCGCGGGGAGAGGCGGTTTGCGTATTGGGCGC
TCTTCCGCTTCCTCGCTCACTGACTCGCTGCGCTCGGTCGTTCGGCTGCGGCGAGCGGTATCAGCTCACT
CAAAGGCGGTAATACGGTTATCCACAGAATCAGGGGATAACGCAGGAAAGAACATGTGAGCAAAAGGCCA
GCAAAAGGCCAGGAACCGTAAAAAGGCCGCGTTGCTGGCGTTTTTCCATAGGCTCCGCCCCCCTGACGAG
CATCACAAAAATCGACGCTCAAGTCAGAGGTGGCGAAACCCGACAGGACTATAAAGATACCAGGCGTTTC
CCCCTGGAAGCTCCCTCGTGCGCTCTCCTGTTCCGACCCTGCCGCTTACCGGATACCTGTCCGCCTTTCT
CCCTTCGGGAAGCGTGGCGCTTTCTCATAGCTCACGCTGTAGGTATCTCAGTTCGGTGTAGGTCGTTCGC
TCCAAGCTGGGCTGTGTGCACGAACCCCCCGTTCAGCCCGACCGCTGCGCCTTATCCGGTAACTATCGTC
TTGAGTCCAACCCGGTAAGACACGACTTATCGCCACTGGCAGCAGCCACTGGTAACAGGATTAGCAGAGC
GAGGTATGTAGGCGGTGCTACAGAGTTCTTGAAGTGGTGGCCTAACTACGGCTACACTAGAAGAACAGTA
TTTGGTATCTGCGCTCTGCTGAAGCCAGTTACCTTCGGAAAAAGAGTTGGTAGCTCTTGATCCGGCAAAC
```

The construct set forth in Table 1 was inserted into the pFB plasmid. Retroviral vector (a modified Moloney murine leukemia virus) prepared using the VIRAPORT® retroviral gene expression system from Stratagene (11011 N. Torrey Pines Road, La Jolla, Calif. 92037 USA). Retroviral supernatant was concentrated for subsequent administration as described further below.

Examples 2-3

Transformation of Ball Pythons

A. Materials and Methods.

Ball python eggs were procured within 24 hours of laying. Subsequently, eggs were candled eggs to locate the embryo which is usually lying on the bottom side of the egg using a fiber optic light. Eggs were placed in a position where the embryo was oriented at the top of the egg.

Mix pFB-hrGFP retroviral supernatant (Stratagene, La Jolla Calif., Catalog number 972002) with polybrene at a final concentration of 10 micrograms per microliter. Inject 100 to 300 microliters of retroviral supernatant with POLYBRENE® cationic polymer (10 micrograms per ml) directly into the embryo that is illuminated using fiber optic lighting using a 30 gauge needle and a 1 cc syringe. Slowly remove the needle and close hole with rubber cement. Turn embryo over, place on top of moist vermiculite and incubate the embryo at a temperature of 88-94° F. for about 60 days, until hatching.

Maintain snakes until shedding and collect skin. One skin was obtained from a non-transgenic ball python as a negative control reaction.

Procedure for DNA extraction of Wild-type Ball Python snake skin: 0.04 grams of skin was chopped with scissors and placed sample in a sterile 1.5 mL micro centrifuge tube. Skin was washed with 1.0 mL of 0.9% NaCl solution, vortexed followed by centrifugation for 10 minutes, at 13.2×1000 rpm, to separate the supernatant from the sample. The supernatant was then removed and 1 mL of cell dispersion solution containing collagenase was added. It has been found that snake cast-off skin reacts to a collagenase treatment (200 mM Tris/HCl buffer (pH 8.0), and 600 units collagenase) thereby increasing the molecular weight of the extracted DNA (Eguchi and Eguchi 2000). This solution was then vortexed to mix contents thoroughly and incubated for 16 hours in a 37° C. shaker incubator at 225 rpm. The suspension was then centrifuged for 10 minutes, at 13.2×1000 rpm and the supernatant discarded. In order to further release the DNA from the snake skin, 1 mL of Proteinase K (10 mM Tris/HCL (pH 8.0), 1 mM EDTA, 1% SDS, and 30 units of Proteinase K) was added to the micro centrifuge tube and incubated for an additional 16 hrs in a 37° C. shaker incubator at 150 rpm. The skin solution was centrifuged for 10 minutes at 13.2×1000 rpm and the supernatant was discarded. Subsequently the DNA was isolated from the solution using Easy-DNA™ Kit (Invitrogen) following protocol #3 from the manual. To isolate the DNA, 350 microliters of Solution A (Isolation Solution—provided with Kit) was added to the pellet, and the mixture was incubated at 65° C. for 10 minutes. Subsequently, 150 microliters of Solution B (precipitation solution-provided with kit) was added to the suspension, and the solution was vortexed for between 10 seconds and 1 minute. 500 microliters of chloroform was added to the suspension and it was vortexed between 10 seconds and one minute. The suspension was placed in the microfuge and microfuged for 20 minutes at the highest speed setting. The upper phase of the solution was removed, placed in a fresh microfuge tube, and mixed with 1 mL of cold (4° C.) 100% ethanol. The solution was incubated for 30 minutes on ice. The solution was microcentrifuged at the top speed of the microfuge for 15 minutes at 4° C. The liquid phase was removed from the DNA pellet, and the DNA pellet was washed with 80% ethanol. The DNA pellet was resuspended in 100 microliters of Tris-EDTA buffer containing 2 mg/ml RNAse A, and incubated at 37° C. for 30 minutes before storage at 4° C. 100 microliters of the DNA was solution was extracted with a concentration of 94.23 ng/ul.

Procedure for DNA extraction of Transgenic Ball Python snake skin: The skin was processed in three sections (⅓ each): Head, Tail, and Mid-section, Dorsal and Ventral sections, a total of six samples.

TABLE 2

Transgenic Snake 1:

|  | Dorsal | Ventral |
| --- | --- | --- |
| Head | 0.03 grams | 0.03 grams |
| Mid-Section | 0.03 grams | 0.04 grams |
| Tail | 0.03 grams | 0.03 grams |

TABLE 3

Transgenic Snake 2:

|  | Dorsal | Ventral |
| --- | --- | --- |
| Head | 0.12 grams | 0.05 grams |
| Mid-Section | 0.10 grams | 0.09 grams |
| Tail | 0.06 grams | 0.06 grams |

The samples were processed using the same procedure as the wild-type DNA extraction procedure.

PCR verification of eGFP in the transgenic Ball-Python DNA: The PCR mixture contained 150 ng of sample DNA, 50 mM Tris-HCL (pH 8.3), 1 mM MgCl2, 100 mM KCL, 3 mg/mL highly purified BSA, 1× Master Amp with Betaine (EPICENTRE®), 2 mM dNTP, 50 pmol of each primer (eGFP-R1 5-TGGCGGATCTTGAAGTTCAC-3, F1 5-TCAAGGAGGACGGCAACATC-3), and 15 U of Taq polymerase. The samples were the amplified using a MJ Research PTC-200 Peltier Thermo Cycler with the following conditions, a hotstart at 95° C. for 3 min, followed by 30 cycles with the following conditions, 95° C. 45 sec, 58° C. 45 sec, 70° C. 1 min 30 sec. The extracted DNA and amplified DNA were analyzed by spectrometry and by 1.2% agarose gel electrophoresis in Tris-Acetate EDTA buffer (TAE). Procedure to verify 118 bp band and 600 bp amplified band: The amplified PCR product using sample Mid-Ventral was fractionated through an agarose gel and the predicted 118 bp band was removed from the gel and cloned into the pGEM-T plasmid using pGEM-T easy kit (Promega, Madison Wis.). The PCR products and linearized plasmid were mixed with the T4 ligase buffer (3 Wiess Units/microliter), and the ligation buffer provided by the kit. The plasmids were introduced into competent bacteria (JM109 Cells) using heat, and grown under ampicillin selection. The plasmid DNA was isolated from bacterial cultures using a QIAfilter™ Plasmid DNA Purification kit (catalog number 12262). The presence of the PCR products in the plasmids were verified by digesting the plasmid with using ECO R1 to verify band insertion. The plasmid was sent to DNA sequencing core facility at the University of Florida to sequence of the insert.

TABLE 4

Blast Results of Insert Compared to Clontech pEGFP vector

```
Score = 229 bits (119), Expect = 5e-56
Identities = 119/119 (100%), Gaps = 0/119 (0%)
Strand = Plus/Plus Query  679 TTCAAGGAGGACGGCAACATCCTGGGGCACAAGCTGGAGTACAACTACAACAGCCACAAC  738
           ||||||||||||||||||||||||||||||||||||||||||||||||||||||||||||
Sbjct   45 TTCAAGGAGGACGGCAACATCCTGGGGCACAAGCTGGAGTACAACTACAACAGCCACAAC  104

Query  739 GTCTATATCATGGCCGACAAGCAGAAGAACGGCATCAAGGTGAACTTCAAGATCCGCCA   797
           |||||||||||||||||||||||||||||||||||||||||||||||||||||||||||
Sbjct  105 GTCTATATCATGGCCGACAAGCAGAAGAACGGCATCAAGGTGAACTTCAAGATCCGCCA   163
```

Query Clontech EGFP vector EGFP between 289 and 1008. Therefore, amplified sequence is within the EGFP gene.

B. Results: Ball Python Experiment.

Five Injected Embryos Hatch from a total of 21 injected (attributed reduced hatchability to novice-level of experience incubating ball python eggs). Incubation conditions are slightly different between a ball python and a corn snake.

Snakes were maintained until skin could be obtained from the natural shedding process and the skin was analyzed for the presence of GFP.

FIG. 1. PCR results from potential Transgenic Ball python skin. All samples indicate a predicted 118 bp PCR product and a 600 bp PCR product. Water control lane shows no amplification products.

Figure 2:
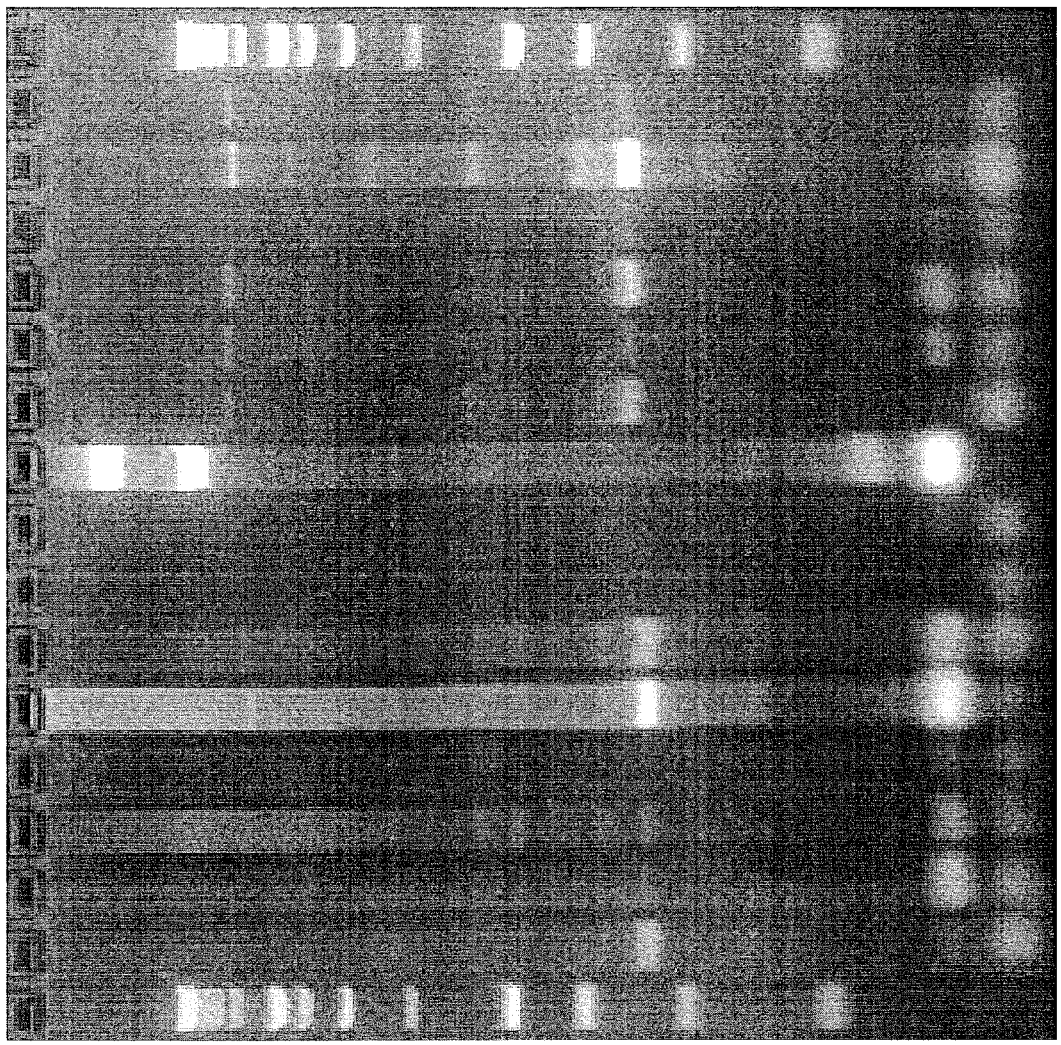
FIG. 2. PCR Results from two transgenic ball pythons (lanes 2-7 and lanes 11-16), positive control plasmid (Lane 10), negative control wild-type ball python DNA (lane 9), and water negative control (lane 10).

FIG. 2. PCR Results from two potential transgenic ball pythons (lanes 2-7 and lanes 11-16), positive control plasmid (Lane 10), negative control wild-type ball python DNA (lane 9), and water negative control (lane 10). FIG. 2 is a repeat of data presented in FIGS. 1 and 3. Therefore, we have identified two animals with GFP DNA in their skin.

Figure 3:
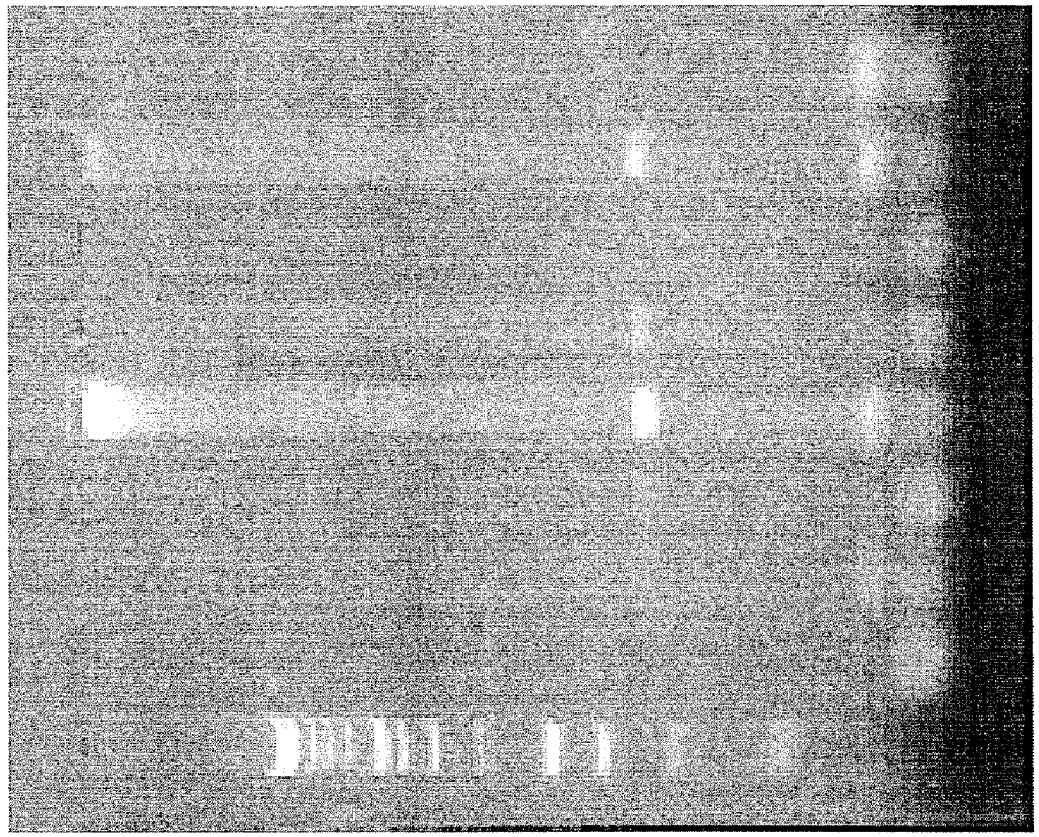
FIG. 3. PCR results from the second transgenic ball python. Lane 1, 1 kb ladder; Lane 2, negative control $dH_2O$; Lane 3, Head—Ventral; Lane 4, Head—Dorsal; Lane 5, Mid-section—Ventral; Lane 6, Mid-section—Dorsal; Lane 7, Tail—Ventral; Lane 8, Tail—Dorsal; Lane 9, Positive control eGFP amplification.

FIG. 3 PCR results from the second transgenic ball python.

Figure 4:
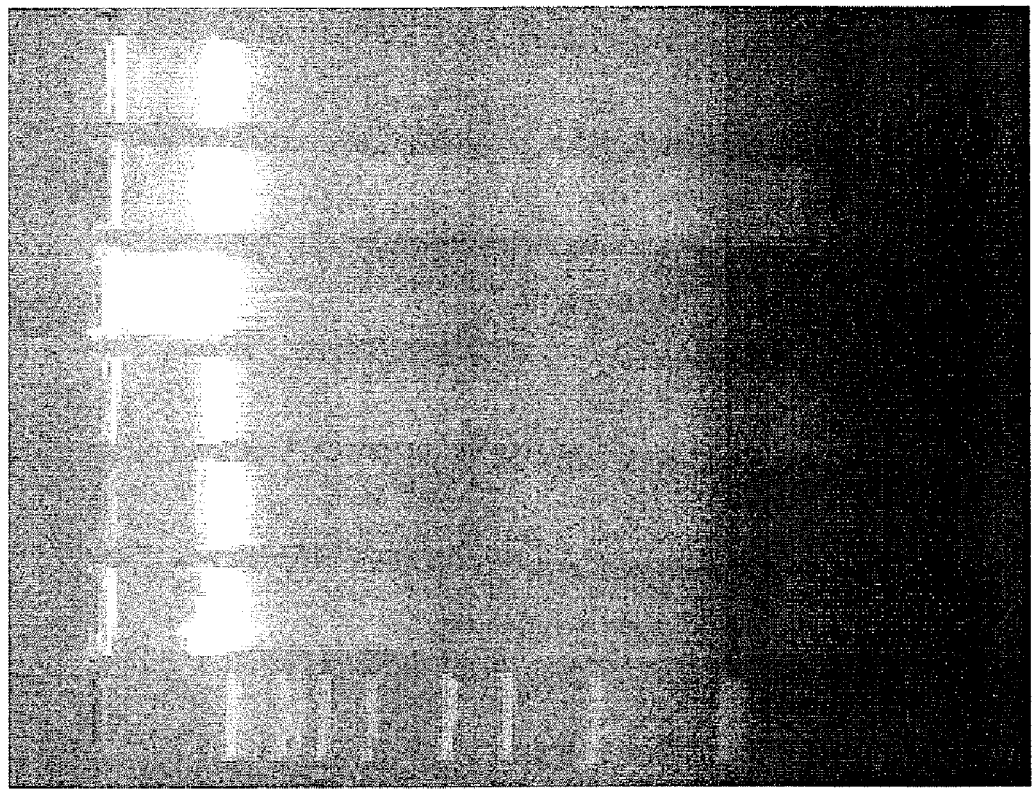
FIG. 4. Verification of DNA integrity of the DNA template used to generate the data presented in FIGS. 1 and 2. Transgenic Ball Python DNA. Lane 1, 1 kb ladder; Lane 2, Head—Ventral; Lane 3, Head—Dorsal; Lane 4, Mid-section—Ventral; Lane 5, Mid-section—Dorsal; Lane 6, Tail—Ventral; Lane 7, Tail—Dorsal.
Figure 5:
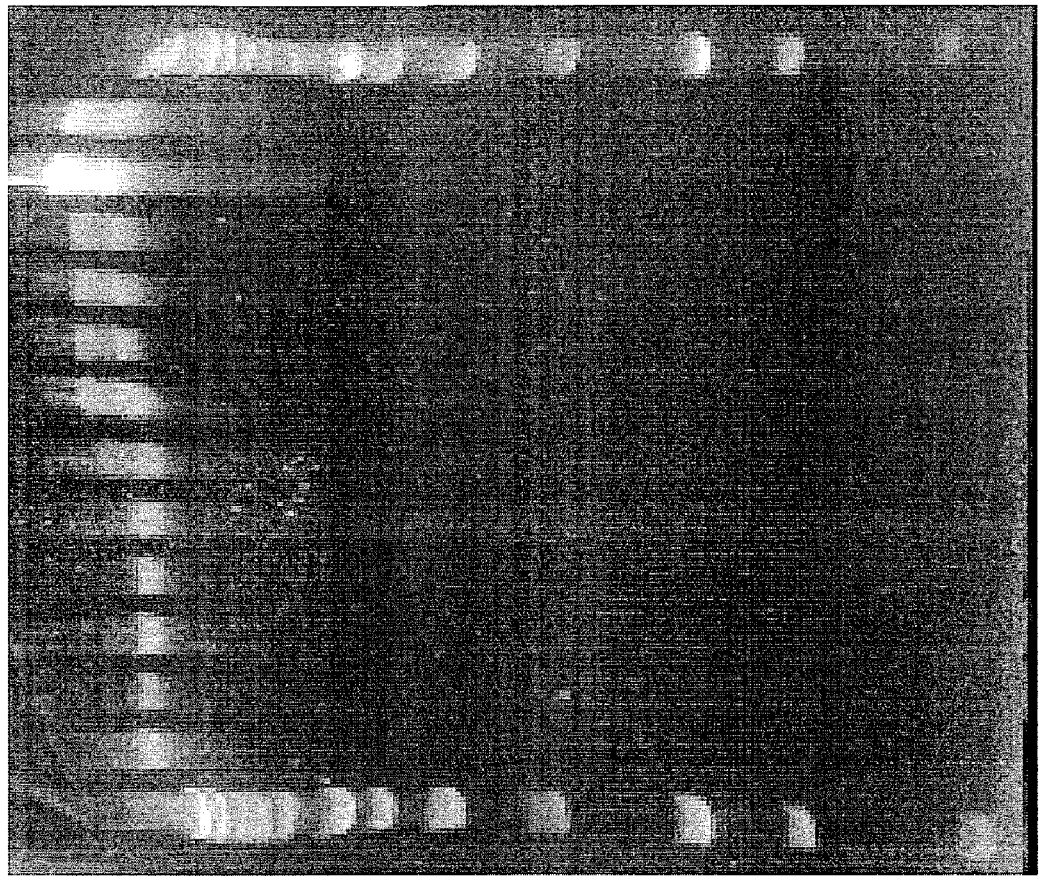
FIG. 5. Verification of DNA integrity of the DNA template used to generate the data presented in FIGS. 1 and 2. Transgenic Ball Python DNA: Lane 1, 1 kb ladder; Lane 2, Head—Dorsal; Lane 3, Head—Dorsal; Lane 4, Mid-section—Dorsal; Lane 5, Mid-section—Dorsal; Lane 6, Tail—Dorsal; Lane 7, Tail—Dorsal; Lane 8, Head—Ventral; Lane 9, Head—Ventral; Lane 10, Mid-section—Ventral; Lane 11, Mid-section—Ventral; Lane 12, Tail—Ventral; Lane 13, Tail—Ventral; Lane 14, 1 kb ladder.

FIGS. 4 and 5 provide verification of DNA integrity of the DNA template used to generate the data presented in FIGS. 1 and 2.

TABLE 5

Blast Results of Insert Compared to Clontech pEGFP vector.

```
Score = 229 bits (119), Expect = 5e-56
Identities = 119/119 (100%), Gaps = 0/119 (0%)
Strand = Plus/Plus Query  679 TTCAAGGAGGACGGCAACATCCTGGGGCACAAGCTGGAGTACAACTACAACAGCCACAAC  738
           ||||||||||||||||||||||||||||||||||||||||||||||||||||||||||||
Sbjct   45 TTCAAGGAGGACGGCAACATCCTGGGGCACAAGCTGGAGTACAACTACAACAGCCACAAC  104

Query  739 GTCTATATCATGGCCGACAAGCAGAAGAACGGCATCAAGGTGAACTTCAAGATCCGCCA  797
           |||||||||||||||||||||||||||||||||||||||||||||||||||||||||||
Sbjct  105 GTCTATATCATGGCCGACAAGCAGAAGAACGGCATCAAGGTGAACTTCAAGATCCGCCA  163
```

Query Clontech EGFP vector EGFP between 289 and 1008. Therefore, amplified sequence is within the EGFP gene.

118 bp from proposed transgenic snake match 100% homology with predicted EGFP sequence.

Example 4

Preparation of FIV Lentiviral Vector

The construct described in Table 1 of example 1 above is inserted into plasmid pCDF1-MCS1 (available from System Biosciences (SBI), 211 South Whisman Road, Mountain View, Calif. 94041 (Tel: 650-968-2200)) and viral particles generated in accordance with known techniques (See Example 1).

Vector is concentrated and used to infect Ball Python in like manner as described in Examples 2-3 above.

Example 5

Transformation of Corn Snakes

Corn snake eggs are obtained and transfected in like manner as described for Ball Python in Examples 1-4 above, but with a slightly smaller injection volume (50-100 microliters).

Experiment #1: Poke hole in egg shell of corn snake eggs with a 30 gauge needle and seal with rubber cement compare manipulated to intact eggs.

Clutch #1 8 total embryos 4 manipulated 4 intact. 3 manipulated hatch and 3 intact hatch.

Clutch #2 15 total embryos. 8 manipulated 7 intact controls. 8 manipulated hatched. 6 intact hatched.

Clutch #3 14 total embryos. 9 manipulated 5 intact controls. 8 manipulated hatch. 5 intact hatch.

Overall Hatch Rate Manipulated 95% Intact 87.5%.

Corn snake eggs are incubated to hatch buried in damp vermiculite particulate media for 55 to 70 days at a temperature of from 72 to 84° F.

Example 6

Transformation of King Snakes

King snake eggs are obtained and transfected in like manner as described for Ball Python in Examples 1-4 above, but with a slightly smaller injection volume.

Specifically retroviral supernatant (pFB system) encoding the eGFP gene derived from the PMIEM plasmid and driven by the RSV/beta-actin/delta-crystallin promoter was generated after transfecting 293T cells. The supernatants were frozen and stored at −80° C. Retroviral supernatent was thawed and mixed with polybrene 10 micrograms per mL supernatent. The supernatent was either concentrated or used as unconcentrated virus. When virus was concentrated, the VIRABIND™ Lentivirus Purification Kit (Cell Biolabs, San Diego Calif.) that employs a purification filter technology was used. The lentivirus purification kit is compatible with both lentiviral and retroviral vectors. Briefly the LTV purification filter is washed with Wash buffer (Catalog 90210), and approximately 10 mL of retroviral cell culture supernatent is applied to the LTV purification filter, the filter is washed with the Wash buffer. Subsequently, the virus was eluted with 2 mL of elution buffer (25 mM Tris pH 7.5, 2.5 mM Mg2Cl, 1 Mm NACl). The embryos were injected with virus suspended in the elution buffer.

12 embryos were injected with approximately 50 microliters of concentrated virus in the first king snake experiment and the site of injection was sealed with rubber cement. Of the 12 that were injected, 4 were incubated through hatching to generate viable offspring. In comparison, six of eight intact control embryos were successfully incubated through hatching. In the second king snake experiment 14 king snake embryos were injected with unconcentrated retroviral supernatent, and the injection site was sealed with paraffin wax. Three of the 14 injected embryos successfully hatched to produce viable offspring. However, zero of six control embryos hatched suggesting that incubation conditions were not optimal.

King snake eggs are incubated to hatch buried in damp vermiculite particulate media for 50 to 65 days at a temperature of from 82 to 85° F.

The foregoing is illustrative of the present invention, and is not to be construed as limiting thereof. The invention is defined by the following claims, with equivalents of the claims to be included therein.

That which is claimed is:

1. A transgenic snake that expresses a heterologous protein expression product, comprising an expression sequence operably linked to a sequence encoding said heterologous expression product, wherein the sequence encoding the expression product is integrated into the genome of the snake, wherein the heterologous protein is expressed in detectable quantities in said snake.

2. The transgenic snake of claim 1, wherein said expression product is a reporter protein.

3. The transgenic snake of claim 1, wherein said expression product is a fluorescent or luminescent protein.

4. The transgenic snake of claim 1, wherein said snake has a phenotype of fluorescence or luminescence not found in the corresponding wild-type snake.

5. The transgenic snake of claim 1, wherein said expression product is a therapeutic protein.

6. The transgenic snake of claim 1, wherein said expression product is expressed in skin, skeletal muscle or both.

7. A transgenic snake that expresses a heterologous protein expression product, comprising an expression sequence operably linked to a sequence encoding said heterologous expression product, wherein the sequence encoding the expression product is integrated into the genome of the snake;

wherein said protein expression product is a fluorescent or luminescent protein expressed in detectable quantities in said snake so that said snake has a phenotype of fluorescence or luminescence not found in the corresponding wild-type snake;

and wherein said snake is a corn snake, ball python, or Kingsnake.

8. The transgenic snake of claim 7, wherein said expression product is expressed in skin, skeletal muscle or both.

9. The transgenic snake of claim 7, wherein said snake is an albino or leucistic snake.

10. A method of screening a compound or composition for snake repellent activity, comprising applying a candidate compound or composition to a target and then observing the behavior of a snake according to claim 8 in relation to said target, wherein avoidance of said target by said snake indicates said compound or composition has snake repellent activity.

11. A method of making a transgenic snake, comprising the steps of:
   (a) providing an expression sequence operably linked to a sequence encoding a heterologous protein expression product,
   (b) transforming a snake in ovo with said expression sequence by injecting directly into a snake embryo a retroviral vector comprising an expression sequence operably linked to a sequence encoding said heterologous protein expression product, so that the sequence encoding the expression product is integrated into the genome of the snake, and then
   (c) incubating said snake to hatch to produce a chimeric first generation snake.

12. The method of claim 11, wherein said expression product is a reporter protein or therapeutic protein.

13. The method of claim 11, wherein said expression product is a fluorescent or luminescent protein and said chimeric first generation snake has a phenotype of fluorescence or luminescence not found in the corresponding wild-type snake.

* * * * *

UNITED STATES PATENT AND TRADEMARK OFFICE
CERTIFICATE OF CORRECTION

| | | |
|---|---|---|
| PATENT NO. | : 7,663,019 B2 | Page 1 of 1 |
| APPLICATION NO. | : 11/752599 | |
| DATED | : February 16, 2010 | |
| INVENTOR(S) | : Mozdziak et al. | |

It is certified that error appears in the above-identified patent and that said Letters Patent is hereby corrected as shown below:

Column 17, Line 11: Please correct "a 600 bp" to read -- a ~600 bp --

Signed and Sealed this

Twenty-seventh Day of July, 2010

David J. Kappos
*Director of the United States Patent and Trademark Office*

SEQUENCE LISTING

```
<160> NUMBER OF SEQ ID NOS: 4

<210> SEQ ID NO 1
<211> LENGTH: 4760
<212> TYPE: DNA
<213> ORGANISM: Artificial
<220> FEATURE:
<223> OTHER INFORMATION: pMIEM construct sequence

<400> SEQUENCE: 1
cagtggggtt ggcactgcca cgctccggat gccgcgctct gatccaaccc cataatcaag      60
ggaacccgaa ttgccccatc attgccccca ccaccccat cctgccgggc cctcacaccc     120
cacgctgcct tctggtgaca ttccccagcc caaacccacg gcttcatggc taccgcgggg    180
catttcccat tgccgcccca ttatcagctc tgcacacctc ccgctgtacc catgcctcgt    240
ggctgcccct ctttgacgta taatcttcta attaataccc ggccttgtca aagtggagca    300
caaacgttaa ttaattcccc agcaggcagg taattaacag tgtgactccc tttttgctgc    360
gagtggggct gatacagaga gatgtggcac tatggagccc acgggtcct ggcactgggt     420 gcccacggag gtccccatgt gcagcttggg agcttgggcc cagctgctcc ctgcttgtgt    480
gttggaggtc gctgagtagt gcgcgagcaa aatttaagct acaacaaggc aaggcttgac    540
cgacaattgc atgaagaatc tgcttagggt taggcgtttt gcgctgcttc gcgatgtacg    600
ggccagatat acgcgtatct gaggggacta gggtgtgttt aggcgaaaag cggggcttcg    660
gttgtacgcg gttaggagtc ccctcaggat atagtagttt cgcttctgca tagggagggg    720
gaaatgtagt cttatgcaat actcttgtag tcttgcaaca tggtaacgat gagttagcaa    780
catgccttac aaggagagaa aaagcaccgt gcatgccgat tggtggaagt aaggtggtac    840
gatcgtgcct tattaggaag gcaacagacg ggtctgacat ggattggacg aaccactgaa    900
ttccgcattg cagagatatt gtatttaagt gcctagctcg atacaataaa cgccatttga    960
ccattcacca cattggtgtg cacctcccaa gctgctcagt gcatgcacgc tcattgccca   1020
tcgctatccc tgcctctcct gctggcgctc cccgggaggt gacttcaagg ggaccgcagg   1080
accacctcgg gggtgggggg agggctgcac acgcggaccc cgctccccct ccccaacaaa   1140
gcactgtgga atcaaaaagg ggggaggggg gatggagggg cgcgtcacac ccccgcccca   1200
caccctcacc tcgaggtgag ccccacgttc tgcttcactc tccccatctc ccccccctcc   1260
ccacccccaa ttttgtattt atttattttt taattatttt gtgcagcgat ggggcgggg    1320 gggggggggg cgcgcgccag gcggggcggg gcggggcgag gggcgggcg gggcgaggcg     1380 gagaggtgcg gcgcagcca atcagagcgg cgcgctccga aagtttcctt ttatggcgag    1440 gcggcggcg cggcggccct ataaaaagcg aagcgcgcgg cgggcgggag tcgctgcgcg     1500
ctgccttcgc cccgtgcccc gctccgccgc cgcctcgcgc cgcccgcccc ggctctgact   1560
gaccgcgtta ctcccacagg tgagcgggcg gacggccct tctcctccgg gctgtaatta    1620
gcgcttggtt taatgacggc tcgtttcttt tctgtggctg cgtgaaagcc ttaaagggct   1680
ccgggagggc cctttgtgcg ggggggagcg gctcggggg tgcgtgcgtg tgtgtgtgcg    1740
tggggagcgc cgcgtgcggc tccgcgctgc ccggcggctg tgagcgctgc gggcgcggcg   1800
cggggctttg tgcgctccgc agtgtgcgcg aggggagcgc ggccggggc ggtgccccgc    1860
```

```
ggtgcggggg ggctgcgagg ggaacaaagg ctgcgtgccg gggtgtgtgc gtgggggggt    1920 gagcagggggg tgtgggcgcg gcggtcgggc tgtaaccccc ccctgcaccc ccctcccccga   1980 gttgctgagc acggcccggc ttcgggtgcg gggctccgtg cggggcgtgg cgcgggggctc    2040 gccgtgccgg gcggggggtg gcggcaggtg ggggtgccgg gcggggcggg gccgcctcgg    2100
gccggggagg gctcggggga ggggcgcggc ggccccccga gcgccggcgg ctgtcgaggc    2160
gcggcgagcc gcagccattg cctttttatgg taatcgtgcg agagggcgca gggacttcct    2220
ttgtcccaaa tctgtgcgga gccgaaatct gggaggcgcc gccgcacccc ctctagcggg    2280
cgcggggcga agcggtgcgg cgccggcagg aaggaaatgg gcggggaggg ccttcgtgcg    2340
tcgccgcgcc gccgtcccct tctccatctc cagcctcggg gctgtccgca gggggacggc    2400
tgccttcggg ggggacgggg cagggcgggg ttcggcttct ggcgtgtgac cggcggggtt    2460
tatatcttcc cttctctgtt cctccgcagc ccccaagctc ccacagtttt acttgaatgt    2520
ggcactgaga gattttttagg agaatatatc aataatgcat ttgaacatat cctttaattt    2580
taattactct caggggggata aacttttggg aggaagattt gttggaagca cagatcccat    2640
catggagatt ctcagctctt ctatatccac tgagcagaga ctgactgaag ttgatgggga    2700
tcgggatcca ccggtcgcca ccatggtgag caagggcgag gagctgttca ccggggtggt    2760
gcccatcctg gtcgagctgg acggcgacgt aaacggccac aagttcagcg tgtccggcga    2820
gggcgagggc gatgccacct acggcaagct gaccctgaag ttcatctgca ccaccggcaa    2880
gctgcccgtg ccctggccca ccctcgtgac caccctgacc tacggcgtgc agtgcttcag    2940
ccgctacccc gaccacatga agcagcacga cttcttcaag tccgccatgc ccgaaggcta    3000
cgtccaggag cgcaccatct tcttcaagga cgacggcaac tacaagaccc gcgccgaggt    3060
gaagttcgag ggcgacaccc tggtgaaccg catcgagctg aagggcatcg acttcaagga    3120
ggacggcaac atcctggggc acaagctgga gtacaactac aacagccaca acgtctatat    3180
catggccgac aagcagaaga acggcatcaa ggtgaacttc aagatccgcc acaacatcga    3240
ggacggcagc gtgcagctcg ccgaccacta ccagcagaac accccatcg cgacggccc    3300 cgtgctgctg cccgacaacc actacctgag cacccagtcc gccctgagca agacccccaa    3360
cgagaagcgc gatcacatgg tcctgctgga gttcgtgacc gccgccggga tcactctcgg    3420
catggacgag ctgtacaagt aaagcggccg cgactctaga tcataatcag ccataccaca    3480
tttgtagagg ttttacttgc tttaaaaaac ctcccacacc tccccctgaa cctgaaacat    3540
aaaatgaatg caattgttgt tgttaacttg tttattgcag cttataatgg ttacaaataa    3600
agcaatagca tcacaaattt cacaaataaa gcatttttttt cactgcattc tagttgtggt    3660
ttgtccaaac tcatcaatgt atcttaaggc gtaaattgta agcgttaatg atccccgggt    3720
accgagctcg aattcgtaat catgtcatag ctgtttcctg tgtgaaattg ttatccgctc    3780
acaattccac acaacatacg agccggaagc ataaagtgta aagcctgggg tgcctaatga    3840
gtgagctaac tcacattaat tgcgttcgc tcactgcccg cttccagtc gggaaacctg      3900 tcgtgccagc tgcattaatg aatcggccaa cgcgcgggga gaggcggttt gcgtattggg    3960
cgctcttccg cttcctcgct cactgactcg ctgcgctcgg tcgttcggct gcgaatgaat    4020
cggccaacgc gcggggagag gcggtttgcg tattgggcgc tcttccgctt cctcgctcac    4080
tgactcgctg cgctcggtcg ttcggctgcg cgagcggta tcagctcact caaaggcgg     4140 aatacggtta tccacagaat caggggataa cgcaggaaag aacatgtgag caaaaggcca    4200
```

```
gcaaaaggcc aggaaccgta aaaaggccgc gttgctggcg ttttttccata ggctccgccc    4260 ccctgacgag catcacaaaa atcgacgctc aagtcagagg tggcgaaacc cgacaggact    4320
ataaagatac caggcgtttc cccctggaag ctccctcgtg cgctctcctg ttccgaccct    4380
gccgcttacc ggatacctgt ccgcctttct cccttcggga agcgtggcgc tttctcatag    4440
ctcacgctgt aggtatctca gttcggtgta ggtcgttcgc tccaagctgg gctgtgtgca    4500 cgaaccccc  gttcagcccg accgctgcgc cttatccggt aactatcgtc ttgagtccaa    4560
cccggtaaga cacgacttat cgccactggc agcagccact ggtaacagga ttagcagagc    4620
gaggtatgta ggcggtgcta cagagttctt gaagtggtgg cctaactacg gctacactag    4680
aagaacagta tttggtatct gcgctctgct gaagccagtt accttcggaa aaagagttgg    4740
tagctcttga tccggcaaac                                                4760

<210> SEQ ID NO 2
<211> LENGTH: 20
<212> TYPE: DNA
<213> ORGANISM: Artificial
<220> FEATURE:
<223> OTHER INFORMATION: PCR primer

<400> SEQUENCE: 2
tggcggatct tgaagttcac                                                  20

<210> SEQ ID NO 3
<211> LENGTH: 20
<212> TYPE: DNA
<213> ORGANISM: Artificial
<220> FEATURE:
<223> OTHER INFORMATION: PCR primer

<400> SEQUENCE: 3
tcaaggagga cggcaacatc                                                  20

<210> SEQ ID NO 4
<211> LENGTH: 119
<212> TYPE: DNA
<213> ORGANISM: Artificial
<220> FEATURE:
<223> OTHER INFORMATION: Amplified PCR product sequence

<400> SEQUENCE: 4
ttcaaggagg acggcaacat cctggggcac aagctggagt acaactacaa cagccacaac      60
gtctatatca tggccgacaa gcagaagaac ggcatcaagg tgaacttcaa gatccgcca      119
```